United States Patent

Prasad et al.

[11] Patent Number: 5,852,202
[45] Date of Patent: Dec. 22, 1998

[54] PROCESS FOR ISOLATING N-(4-FLUOROPHENYL)-N-(1-METHYLETHYL)-2-[(5-TRIFLUOROMETHYL)-1,3,4-THIADIAZOL-2-YL)OXY]ACETAMIDE

[75] Inventors: Vidyanatha A. Prasad, Leawood, Kans.; Jonathan D. Spicher, Parkville; Warren A. Fischer, Blue Springs, both of Mo.

[73] Assignee: Bayer Corporation, Pittsburgh, Pa.

[21] Appl. No.: 989,486

[22] Filed: Dec. 12, 1997

[51] Int. Cl.$^6$ .................................................. C07D 285/13
[52] U.S. Cl. .............................................................. 548/136
[58] Field of Search ............................................... 548/136

[56] References Cited

U.S. PATENT DOCUMENTS

| | | | |
|---|---|---|---|
| 4,585,471 | 4/1986 | Förster et al. | 71/90 |
| 4,645,525 | 2/1987 | Förster et al. | 71/88 |
| 4,756,741 | 7/1988 | Förster et al. | 71/90 |
| 4,968,342 | 11/1990 | Förster et al. | 71/90 |
| 5,090,991 | 2/1992 | Förster et al. | 71/90 |
| 5,101,034 | 3/1992 | Schmidt et al. | 548/136 |

*Primary Examiner*—Robert Gerstl
*Attorney, Agent, or Firm*—Joseph C. Gil; Carol Marmo

[57] ABSTRACT

The present invention relates to a process for isolating N-(4-fluorophenyl)-N-(1-methylethyl)-2-[(5-trifluoromethyl)-1,3,4-thiadiazol-2-yl)oxy]acetamide from a solution of N-(4-fluorophenyl)-N-(1-methylethyl)-2-[(5-trifluoromethyl)-1,3,4-thiadiazol-2-yl)oxy]acetamide in an aprotic, aromatic solvent. The process includes the steps of: (a) removing the solvent from the solution to form a substantially solvent-free material; (b) melting the material from step (a) to form a molten material; and (c) isolating N-(4-fluorophenyl)-N-(1-methylethyl)-2-[(5-trifluoromethyl)-1,3,4-thiadiazol-2-yl)oxy]acetamide from the molten material by flaking.

16 Claims, No Drawings

PROCESS FOR ISOLATING N-(4-FLUOROPHENYL)-N-(1-METHYLETHYL)-2-[(5-TRIFLUOROMETHYL)-1,3,4-THIADIAZOL-2-YL)OXY]ACETAMIDE

TECHNICAL FIELD OF THE INVENTION

The field of this invention is the synthesis of acetamide herbicides. More particularly, this invention relates to processes for making, recovering and isolating N-(4-fluorophenyl)-N-(1-methylethyl)-2-[(5-trifluoromethyl)-1,3,4-thiadiazol-2-yl)oxy]acetamide.

BACKGROUND OF THE INVENTION

Certain azolyloxy-carboxylic acid amides and heteroaryloxy-acetamides of the general formula R-O-CH ($R^1$)-CO-N($R^2$)($R^3$) are known to have herbicidal activity (See, e.g., U.S. Pat. Nos. 4,756,741 and 5,101,034). U.S. Pat. No. 5,101,034 discloses a particular class of heteroaryloxyacetamides, namely thiadiazole acetamides as having herbicidal activity. The thiadiazole acetamides are made by reacting a thiadiazole sulfone with an hydroxyacetanilide in acetone. Of particular relevance to the present invention is the disclosure of a synthetic scheme for making 2-(5-trifluoromethyl)-1,3,4-thiadiazole-2-yl-oxy)-N-methylacetanilide. In accordance with that synthetic scheme, 2-methylsulfonyl-5-trifluoromethyl-1,3,4-thiadiazole is reacted with N-methyl-2-hydroxyacetanilide, potassium carbonate, and tetraethylammonium bromide. Acetone is used as the solvent for the reaction. The reaction is carried out at a temperature of 20° C.–25° C. for 20 hours. Undissolved salts are filtered off and washed with acetone. The filtrate is freed of solvent in vacuo and the resulting residue taken up in diethyl ether, washed with dilute hydrochloric acid, dried and filtered. After freeing the filtrate of solvent, the end product is crystallized from the oily residue. Reported yields are about 90%.

U.S. Pat. Nos. 4,756,741 and 4,645,525 disclose a synthetic scheme for making O-(2-trifluoromethyl-1,3,4,-thiadiazol-5-yl-oxo)acetic-N-methylanilide. In accordance with that scheme, 2-hydroxyacetic acid-N-methylanilide is reacted with dimethylsulfoxide and calcium oxide at 50° C. for 1 hour. 5-Bromo-2-trifluoromethyl-1,3,4-thiadiazole is then added to the reaction mixture and the mixture stirred at 50° C. for 40 hours. The mixture is then poured into water and the oil that precipitates is extracted with methylene chloride. The end product is obtained in about 90% yield by distilling off the methylene chloride.

U.S. Pat. No. 4,585,471 discloses synthetic schemes for making (5-trifluoromethyl-1,3,4-thiadiazol-2-yl-oxy)-acetic acid 2-ethylpiperidine and (5-trifluoromethyl-1,3,4-thiadiazol-2-yl-oxy)-acetic acid 2-methylpiperidine. In accordance with those synthetic schemes, the ethylpiperidine compound is made by reacting hydroxyacetic acid-2-ethylpiperidine with 2-chloro-5-trifluoromethyl-1,3,4-thiadiazole in the presence of potassium tert-butanate in tert-butanol at a temperature of 20° C. to 30° C. for 3 hours and the methylpiperidine compound is made by reacting 2-chloro-5-trifluoromethyl-1,3,4-thiadiazole in toluene with hydroxyacetic acid-2-methylpiperidine in the presence of sodium hydroxide. The end product, in both cases, is recovered from the reaction mixture by acidification with hydrochloric acid, drying, removal of solvent and crystallization. The reported yields of the end-products were 66% (ethylpiperidine) and 54% (methylpiperidine).

U.S. Pat. Nos. 4,968,342 and 5,090,991 disclose a synthetic scheme for making N-isopropyl-(5-trifluoromethyl-1,3,4,-thiadiazol-2-yl)-3'-chlorooxyacetanilide. In accordance with that scheme, 2-methylsulfonyl-5-trifluoromethyl-1,3,4-thiadiazole, dissolved in acetone, is reacted with 3'-chloro-N-isopropylhydroxyacetanilide in the presence of sodium hydroxide and water for 3 hours at −20° C. Water is added to the reaction mixture and the crystalline end-product obtained by crystallization in 85% yield.

It can be seen from the above, that existing methods for making acetamide herbicides suffer from low yields (54% to 85%), prolonged reaction times (20 to 40 hours) or the use of problematic solvents (acetone). There continues to be a need in the art, therefore, for a practical method for making these herbicides, which method avoids the problems of the existing art.

BRIEF SUMMARY OF THE INVENTION

In one aspect, the present invention provides a process for isolating N-(4-fluorophenyl)-N-(1-methylethyl)-2-[(5-trifluoromethyl)-1,3,4-thiadiazol-2-yl)oxy]acetamide (fluthiamide) from a solution of N-(4-fluorophenyl)-N-(1-methylethyl)-2-[(5-trifluoromethyl)-1,3,4-thiadiazol-2-yl) oxy]acetamide in an aprotic, aromatic solvent. In accordance with the process, the solvent is removed from the solution to form a substantially solvent-free material, the solvent-free material is melted to form a molten material and N-(4-fluorophenyl)-N-(1-methylethyl)-2-[(5-trifluoromethyl)-1, 3,4-thiadiazol-2-yl)oxy]acetamide is isolated from the molten material by flaking.

The solvent is preferably toluene, cumene, xylene or mesitylene and, more preferably toluene. The solvent can be removed using any means well known in the art. In one embodiment, the solvent is evaporated under a negative pressure (i.e., partial vacuum). The molten material can be obtained directly via solvent removal at temperature of from about 70° C. to about 85° C. during evaporation. A temperature of from about 75° C. to about 80° C. is preferred.

N-(4-Fluorophenyl)-N-(1-methylethyl)-2-[(5-trifluoromethyl)-1,3,4-thiadiazol-2-yl)oxy]acetamide is isolated from the molten material by flaking. Flaking can be carried out using any flaking apparatus well known in the art. In a preferred embodiment, the molten material from step (b) of the process is spread out on a solid surface, cooled to a temperature of from about 20° C. to about 30° C., and maintained at that temperature until crystallization of N-(4-fluorophenyl)-N-(1-methylethyl)-2-[(5-trifluoromethyl)-1, 3,4-thiadiazol-2-yl)oxy]acetamide occurs.

The solution of N-(4-fluorophenyl)-N-(1-methylethyl)-2-[(5-trifluoromethyl)-1,3,4-thiadiazol-2-yl)oxy]acetamide in solvent can be acidified before solvent removal. Acidification is accomplished by treating the solution with a mineral acid to a pH of from about 1 to about 5.

N-(4-Fluorophenyl)-N-(1-methylethyl)-2-[(5-trifluoromethyl)-1,3,4-thiadiazol-2-yl)oxy]acetamide prepared by any process can be used in the isolation method. In a preferred embodiment, the solution of N-(4-fluorophenyl)-N-(1-methylethyl)-2-[(5-trifluoromethyl)-1,3,4-thiadiazol-2-yl)oxy]acetamide is prepared by a process that includes the steps of: (a) reacting 2-(methylsulfonyl)-5-(trifluoromethyl)-1,3,4-thiadiazole with N-(4-fluorophenyl)-2-hydroxy-N-(1-methylethyl)acetamide in an aprotic, aromatic solvent in the presence of an aqueous alkali to form a reaction product having an aqueous phase and an organic phase that contains the N-(4-fluorophenyl)-N-(1-methylethyl)-2-[(5-trifluoromethyl)-1,3,4-thiadiazol-2-yl) oxy]acetamide; and (b) separating the aqueous and organic phases to provide the solution. Before separating the phases, the reaction product can be acidified by treatment with a mineral acid. A mineral acid such as sulfuric or hydrochloric acid is added to the reaction mixture until the pH of that product reaches a level of from about 1 to about 6.

DETAILED DESCRIPTION OF THE INVENTION

I. The Invention

The present invention relates to processes for the synthesis, recovery and isolation of the herbicide, N-(4-fluorophenyl)-N-(1-methylethyl)-2-[(5-trifluoromethyl)-1,3,4-thiadiazol-2-yl)oxy]acetamide. The process includes the step of reacting 2-(methylsulfonyl)-5-(trifluoromethyl)-1,3,4-thiadiazole with N-(4-fluorophenyl)-2-hydroxy-N-(1-methylethyl)acetamide in an aprotic, aromatic solvent. Formed N-(4-fluorophenyl)-N-(1-methylethyl)-2-[(5-trifluoromethyl)-1,3,4-thiadiazol-2-yl)oxy]acetamide can be recovered via phase separation and solvent removal. Isolation is accomplished using flaking.

II. Isolation of N-(4-fluorophenyl)-N-(1-methylethyl)-2-[(5-trifluoromethyl)-1,3,4-thiadiazole-2-yl)oxy]acetamide Using Flaking The present invention provides a process for isolating N-(4-fluorophenyl)-N-(1-methylethyl)-2-[(5-trifluoromethyl)-1,3,4-thiadiazol-2-yl)oxy]acetamide. In accordance with this process, N-(4-fluorophenyl)-N-(1-methylethyl)-2-[(5-trifluoromethyl)-1,3,4-thiadiazol-2-yl)oxy]acetamide, obtained by any means, is in a solvent such as toluene. The solvent is removed via evaporation and the solid product is isolated from its molten form via flaking operation. As used herein, the term "flaking" means, as is well known in the art, solidification or crystallization. Flaking is typically accomplished by removing the solvent from the solution of N-(4-fluorophenyl)-N-(1-methylethyl)-2-[(5-trifluoromethyl)-1,3,4-thiadiazol-2-yl)oxy]acetamide to form a substantially solvent-free material, melting the solvent-free material to form a molten material, spreading the molten material out on a solid surface and allowing the product to crystallize from the molten material.

Solvent can be removed from the solution using any means well known in the art. Preferably, solvent evaporation is preformed under a negative pressure using a vacuum apparatus or by a steam distillation. It is desirable that the product not be allowed to solidify during evaporation. Therefore, evaporation typically occurs at a temperature of from about 60° C. to about 85° C. More preferably, the temperature is maintained between about 70° C. and about 80° C. By maintaining the temperature in this range during evaporation, the desired product is formed as a molten material. The molten material is then spread out in a thin layer on a solid surface, cooled to a temperature of from about 20° C. to about 30° C. (room temperature) and maintained at that temperature until crystallization. The product crystallizes as aggregates of flakes on the cooled solid surface.

Flaking is typically accomplished on a single drum flaker equipped with a chrome-plated cast iron drum and an application roll preferably made of stainless steel. The material to be fed into the flaker is maintained at a temperature of from about 70° C. to 100° C., preferably, at a temperature of from about 80° C. to about 90° C. and, even more preferably at a temperature of from about 80° C. to about 85° C. The flaker drum is maintained at a temperature of from about 5° C. to about 60° C. and preferably at a temperature of from about 10° C. to about 50° C. Flaker drum speed is maintained at a level of from about 0.5 to about 2.0 RPM, preferably at a speed of from about 0.7 to about 1.6 RPM. The application roll is maintained at a temperature of from about 10° C. to about 95° C. a/nd preferably at a temperature of from about 50° C. to about 70° C. The application roll speed is preferably maintained at a speed of from about 100 to about 250 RPM and, more preferably at a speed of about 190 RPM.

Flake thickness is preferably from about 0.04 inches to about 0.08 inches. Flake size within the preferred range can be increased by decreasing the drum temperature and drum speed. Flake thickness can be decreased by decreasing the agitator roll speed. The overall flaking production rate can be increased by increasing agitator roll speed and drum speed.

EXAMPLE 1

Synthesis of N-(4-fluorophenyl)-N-(1-methylethyl)-2-(5-trifluoromethyl)-1,3,4-thiadiazol-2-yl)oxy] acetamide (Fluthiamide)

A 2 liter, 4-necked round bottom flask containing 632.2 g of a TDA-sulfone suspension in toluene (1.0M of ca. 99% A.I. TDA-sulfone, on a solvent-free basis) was fitted with an overhead stirrer, thermometer, 250 ml barostatic addition funnel and a dry ice acetone bath. The toluene TDA-sulfone slurry was cooled to 0° C. with agitation. 415.7 g of a FOE-hydroxy solution in toluene (1.0M of ca. 98% A.I. FOE-hydroxy on a solvent-free basis) was added to the TDA-sulfone slurry in toluene with agitation at 0°–5° C. The amount of toluene required for the reaction can be reduced by about 50% if solid TDA-sulfone is used instead of a TDA-sulfone suspension in toluene.

A 25% NaOH solution was added to the reaction mixture over a period of 1 to 5 hours at 0° to 5° C. under constant agitation. The addition of NaOH can be done over various times (1 hr, 1.5 hr, 2 hr at 0°–5° C.) without adverse results. The entire mixture was cooked for 1 hr at 0°–5° C.; a sample of the toluene phase was then tested for completion of reaction via gc analysis. Analysis indicated a 2.8% deficiency of TDA-sulfone, which was made up by adding a measured amount of TDA-sulfone. The reaction was complete after an additional half hour of cooking at 0°–5° C.

The entire mixture was transferred to a separator funnel and the phases were separated at 0°–10° C. The aqueous phase was extracted with two portions of toluene (about 50 g each portion). The organic phases were all combined and treated with about 1 g of conc. HCl (pH 4.5). The solvent toluene was stripped by means of a rotary evaporator under water aspirator vacuum (ca. 20 mm Hg) using a maximum bath temperature of 80° C. It is important to adjust the vacuum so that toluene is removed gradually (not too rapidly) at 75°–80° C. bath temperature to prevent solidification of fluthiamide during the solvent removal step. The molten product was poured onto an enamel pan and allowed to flake. The flaked material was crushed and dried under vacuum at ambient temperature. Fluthiamide was produced with a purity of 98.2% and a net yield (N.Y.) of 93.2%, based on TDA-sulfone.

In additional studies, the effects of reaction temperature and FOE-hydroxy purity on fluthiamide production were tested. The procedures used were the same as set forth above. The results of these studies are summarized in the tables, below.

| Exper # | Rxn Temp (°C.) | Fluthiamide A.I. (%) | Net Yield based on FOE-Chloride (%) |
|---|---|---|---|
| 1 | 0–5 | 98.2 | 95.5 |
| 2 | 5–10 | 98 | 95.1 |
| 3 | 10–15 | 98.1 | 94.7 |
| 4 | 15–20 | 97.8 | 94 |
| 4 | 20–30 | 96.8 | 93.6 |

It can be seen from the data in the table, above, that fluthiamide purity and net yield decreased with increasing reaction temperatures over the range of 0° C. to 30° C.

| Exper # | FOE-Hydroxy A.I. (%) | Fluthiamide A.I. (%) | Net Yield Based on FOE-Chloride* (%) |
|---|---|---|---|
| 1 | 98.2 | 98.2 | 95.5 |
| 2 | 97.3 | 96.8 | 94.8 |
| 3 | 96.4 | 95.5 | 93.5 |
| 4 | 95.2 | 95.1 | 93.4 |
| 5 | 94.8 | 94.3 | 93.2 |

*-FOE chloride is the precursor to FOE hydroxy

The data in the table above show that fluthiamide purity and yield are directly proportional to the purity of FOE-hydroxy used in the reaction.

EXAMPLE 2

Recovery of Fluthiamide Using Acid After Separation

TDA-Sulfone (0.1 mol), FOE-hydroxy (0.1 mol) and toluene (0.434 mol) were added to a reaction vessel, mixed and cooled to a temperature of 0° C. to 5° C. An aqueous solution of NaOH (50 weight percent; 0.15 mol) was slowly added to the cooled mixture over 1 hour. The mixture was maintained at 0° C. to 5° C. for an additional hour.

The mixture was then acidified to a pH of about 5.2 with HCl. The aqueous and organic phases were separated. The organic phase was acidified to a pH of about 5.5 with HCl. Fluthiamide was isolated from the acidified organic phase using the flaking procedure set forth above.

EXAMPLE 3

Preparation of Fluthiamide Using Base and Acid Before Phase Separation

Embodiment 1

0.25 Moles of TDA-sulfone, 0.25 moles of FOE-hydroxy and 1.085 moles of toluene were mixed together and cooled to 5° C. 0.3 Moles of sodium hydroxide in the form of a 40 weight percent solution was added to the reaction mixture over a 1 hour period of time. The temperature of the reaction mixture was maintained between 5° C. and 10° C. for about 2 hours. The resulting reaction mixture was acidified to a pH of 5.0 with 10 weight percent HCl. The aqueous and organic layers were separated. The aqueous layer was extracted with toluene and the toluene extract added to the organic layer. The final product, fluthiamide, was isolated using flaking after removal of the toluene. Fluthiamide produced in accordance with this embodiment had a purity of 97.1% A.I. and a net yield of 99%.

Embodiment 2

About 17 moles of toluene, 3 moles of TDA-sulfone and 3 moles of FOE- hydroxy were mixed together and cooled to a temperature of 5° C. 450 ml of a 25 weight percent aqueous solution of sodium hydroxide was added to the mixture over a 1 hour period of time. About 270 ml of water and 85.8 grams of a 70 weight percent solution of $H_2SO_4$ were added to the reaction mixture to decrease the pH from a value of 13 to a value of 2.8. The reaction mixture was then heated to a temperature of 45° C. and held at that temperature for 15 minutes. The reaction mixture was stirred and heated to 65° C. for about 30 minutes. 50 mls of water was added to the mixture and the mixture heated to 85° C. After two hours, the reaction mixture was filtered and the aqueous and organic phases separated. Toluene was stripped off the organic layer and fluthiamide isolated using flaking. Fluthiamide prepared in accordance with this embodiment had a purity of 99.3% A.I. and a net yield of 99.6%.

Embodiment 3

About 3 moles of toluene, 0.5 moles of TDA-sulfone and 0.5 moles of FOE-hydroxy were mixed together and cooled to a temperature to a 5° C. 96 Grams of a 25 weight percent sodium hydroxide solution was added over a period of time of 1 hour while maintaining the temperature at 5° C. Following the addition of sodium hydroxide, the reaction mixture was heated for an additional 1.5 hours at 5° C. The reaction mixture was then titrated with 16.3 grams of concentrated HCl and quenched with 55 grams of water. Following the addition of acid and water, the reaction mixture was heated to a temperature of 45° C. for 1.5 hours. The temperature was then increased to 65° C. and maintained at this temperature for an additional 35 minutes. The temperature of the reaction mixture was then increased to 85° C. and maintained at this temperature for about 15 to 20 minutes. The reaction mixture was cooled, filtered, and the organic and aqueous layers were separated. Fluthiamide was isolated from the organic layer by distilling off the toluene and isolating fluthiamide using flaking. When prepared in accordance with this embodiment, fluthiamide had a purity of 96.9% A.I. and a net yield of 97.7%.

EXAMPLE 4

Recovery of Fluthiamide with Flaking

Batches of fluthiamide were prepared from FOE hydroxy, TDA sulfone and toluene using aqueous alkali using the reaction conditions summarized below.

Toluene/FOE-hydroxy Mole Ratio 6.00

TDA-sulfone/FOE-hydroxy Mole Ratio 1.00–1.03

NaOH/FOE-hydroxy Mole Ratio 1.30–1.35

NaOH Add Time 3 hours

Reaction Temperature 5°–15° C.

Cook Time 0–1 hour

In other batches, FOE hydroxy was washed with sulfuric acid under the conditions summarized below:

Initial Toluene/FOE-hydroxy Mole Ratio 1.36

70% $H_2SO_4$/FOE-hydroxy Mole Ratio 0.08

Final Toluene/FOE-hydroxy Mole Ratio 8.2–8.8

TDA-sulfone/FOE-hydroxy Mole Ratio 1.00–1.03

NaOH/FOE-hydroxy Mole Ratio 1.30–1.35

NaOH Concentration 50 wt. %

NaOH Add Time 3 hours

Reaction Temperature 5°–15° C.

Cook Time 0–1 hour

In all batches, phase separation was accomplished using the conditions summarized below.

$H_2O$/FOE-hydroxy Ratio 1.10

Phase Separation pH 12–14

Phase Separation Temp 20° C.

Filtration no

Mode batch

After phase separation, the fluthiamide was acidified to pH 2 to 4 and transferred to the stripper feed tank. Fluthiamide was isolated as follows.

Toluene was removed by a continuous atmospheric steam strip in a packed column, leaving a molten fluthiamide/mother liquor mixture. The toluene was then recycled to the TDA-sulfone and fluthiamide reactions. The accumulated fluthiamide/aqueous phase was allowed to phase separate and then solidified on a 24"×24" pilot flaker unit using the conditions set forth below.

Drum Speed 0.6–2.0 rpm

Roll Speed 150 to 200 RPM

Drum Temperature 5° C. to 60° C.

Roll Temperature 10° C. to 95° C.

The % AI for fluthiamide made using these procedures ranged from about 92% A.I. to about 99% A.I.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for isolating N-(4-fluorophenyl)-N-(1-methylethyl)-2-[(5-trifluoromethyl)-1,3,4-thiadiazol-2-yl)oxy]acetamide from a solution of N-(4-fluorophenyl)-N-(1-methylethyl)-2-[(5-trifluoromethyl)-1,3,4-thiadiazol-2-yl)oxy]acetamide in an aprotic, aromatic solvent, comprising the steps of:

(a) removing the solvent from the solution to form a substantially solvent-free material;

(b) melting the material from step (a) to form a molten material; and (c) isolating N-(4-fluorophenyl)-N-(1-methylethyl)-2-[(5-trifluoromethyl)-1,3,4-thiadiazol-2-yl)oxy]acetamide from the molten material by flaking.

2. The process of claim 1 wherein the solvent is toluene, cumene, xylene or mesitylene.

3. The process of claim 2 wherein the solvent is toluene.

4. The process of claim 1 wherein the solvent is removed via steam distillation.

5. The process of claim 1 wherein the solvent is removed by evaporation.

6. The process of claim 5 wherein the solvent is evaporated under negative pressure.

7. The process of claim 6 wherein the solvent is evaporated under negative pressure at a temperature of from about 70° C. to about 85° C.

8. The process of claim 7 wherein the temperature is from about 75° C. to about 80° C.

9. The process of claim 1 wherein the molten material from step (b) is spread out on a solid surface, cooled to a temperature of from about 5° C. to about 60° C., and maintained at that temperature until crystallization of N-(4-fluorophenyl)-N-(1-methylethyl)-2-[(5-trifluoromethyl)-1,3,4-thiadiazol-2-yl)oxy]acetamide occurs.

10. The process of claim 9 wherein the temperature is about 10° C. to about 50° C.

11. The process of claim 1 wherein the solution of N-(4-fluorophenyl)-N-(1-methylethyl)-2-[(5-trifluoromethyl)-1,3,4-thiadiazol-2-yl)oxy]acetamide is prepared by a process comprising the steps of:

(a) reacting 2-(methylsulfonyl)-5-(trifluoromethyl)-1,3,4-thiadiazole with N-(4-fluorophenyl)-2-hydroxy-N-(1-methylethyl)acetamide in the aprotic, aromatic solvent in the presence of an aqueous alkali to form a reaction mixture having an aqueous phase and an organic phase that contains the N-(4-fluorophenyl)-N-(1-methylethyl)-2-[(5-trifluoromethyl)-1,3,4-thiadiazol-2-yl)oxy]acetamide; and (b) separating the aqueous and organic phases.

12. The process of claim 11 further comprising the step of acidifying the reaction mixture before separating the phases.

13. The process of claim 12 wherein the reaction mixture is treated to a pH of from about 1 to about 6 with a mineral acid.

14. The process of claim 13 wherein the mineral acid is hydrochloric acid or sulfuric acid.

15. The process of claim 11 further comprising the step of acidifying the organic phase after separation from the aqueous phase and before removing the solvent.

16. The process of claim 15 wherein the organic phase is acidified to a pH of from about 2 to about 5 with sulfuric or hydrochloric acid.

* * * * *